United States Patent [19]

Paques et al.

[11] Patent Number: 4,960,703
[45] Date of Patent: Oct. 2, 1990

[54] COMPOSITION FOR IN VITRO MICROPROPAGATION OF PLANTS

[75] Inventors: Marc Paques, Jambes; Emile P. Boxus, Brussels, both of Belgium

[73] Assignee: Personnalite Juridique de la Station des Cultures Fruitieres et Maraicheres, Gembloux, Belgium

[21] Appl. No.: 41,427

[22] Filed: Mar. 23, 1987

[30] Foreign Application Priority Data

Apr. 23, 1986 [BE] Belgium ......................... 0/216.580

[51] Int. Cl.$^5$ ............................................. C12N 5/00
[52] U.S. Cl. ........................... 435/240.45; 435/240.4; 435/240.54
[58] Field of Search ........... 435/240.4, 240.49, 240.54, 435/240.51, 240.45

[56] References Cited

U.S. PATENT DOCUMENTS

3,959,251  5/1976  Porath et al. ..................... 435/178
4,248,971  2/1981  Youssef ............................ 435/253

FOREIGN PATENT DOCUMENTS

0129668   4/1984  European Pat. Off.
2099851  12/1982  United Kingdom.

OTHER PUBLICATIONS

Derbergh, P., 1983, Physiol. Plant, 59:270-276.
Paques, M. and Boxus, Ph., "Vitrification": Review of Literature, Acta Horiculturae 212, 1987, pp. 155-156.
M. Pacques and Ph. Boxus, A Model to Learn "Vitrification", The Rootstock Apple M.26 present Results, Acta Horticulturae 212, 1987, pp. 193-210.
Edwin F. George, Ph.D. and Paul D. Sherrington MSc, Plant Propagation by Tissue Culture, Handbook and Directory of Commercial Laboratories, 1984.
*Colloque International,* (1981), pp. 101-108, "La Micropropagation du Merisier A Partir de la Culture de Meristeme", P. Druart et al.
*Bull. Rech. Agron. Gembloux,* (1974), pp. 189-192, "Premiers Resultats Obtenus Dans la Culture 'In Vitro' du Meristeme Apical de Sujets Porte . . . "M. Quoirin.
*Bull. Rech. Agron. Gembloux,* (1971), pp. 3-5, "La Culture de Meristemes de Prunus. Note Preliminaire Relative A l'Espece P. Pandora", P. Boxus.
*Handbook and Directory of Commercial Laboratories,* (1984) "Plant and Propagation by Tissue Culture", E. George et al.
*Acta Horticulturae,* (1987), vol. 212, pp. 155-166, "Vitrification": Review of Literature, M. Paques and Boxus.
*Acta Horticulturae,* (1987), vol. 212, pp. 193-210, "A Model to Learn 'Vitrification' The Rootstock Apple M.26 Present Results", M. Paques and Boxus.
*Molecular Biology of the Gene,* vol. 2, "Crop Improvement Through Genetic Engineering", James D. Watson, et al.

*Primary Examiner*—Charles F. Warren
*Assistant Examiner*—David T. Fox
*Attorney, Agent, or Firm*—Oblon, Spivak, McClelland, Maier & Neustadt

[57] ABSTRACT

The invention relates to a culture medium containing an effective amount of agar hydrolysate. This material is advantageously used to fight against the appearance of the plant vitrification phenomenon during in vitro micropropagation of plants.

9 Claims, No Drawings

COMPOSITION FOR IN VITRO MICROPROPAGATION OF PLANTS

BACKGROUND OF THE INVENTION

1. Field of the Invention

The invention relates to the in vitro multiplication of plants.

2. Discussion of the Background

Plants which are multiplied in vitro tend to display growth disturbances which disrupt the industrial production of these plants by micropropagation. The affected explants (offshoots) bear abnormal leaves that are more or less rolled up, translucid, often displaying a dark green color. The explants lose their capacity to proliferate, they canker and die more or less rapidly.

This problem is most often called "vitrification", "vitrescence" or "hyperhydria", and it will be referred to hereafter as "vitrification". This phenomena is all the more frequent or severe when the plants are subjected to intense multiplication.

The use of liquid media also increases the risks of vitrification. NAVATEL (Fruits, vol. 37, n° 5, pp. 331-336, 1982) described the problem as follows: "This symptom which generally appears during the multiplication phase has been noted by many laboratories. The microcuttings or microplants adopt a "vitreous" aspect. The leaves which are dark green and shiny, bend, and become brittle and translucid. The significance of the damage appears to increase with the number of cultures grown on the proliferation medium which has a high cytokinine content. In most cases, the seedlings which display those symptoms become stymied and they are nearly no longer usable for subsequent multiplication. Sometimes we observe a certain restoration of the plant when it is placed in a medium free of auxine and cytokinine. This kind of phenomena has been observed on the GF 677 and also on various stocks from cherry-trees and appletrees.

"Many hypotheses have been set forth to try to explain the origin of these symptoms; too rich a medium, toxicity of the $NH_4^+$ ion, excessive density inside the jar, ethylene production, ill adaptation of the culture jars, toxicity by way of accumulation of specific growth substances (cytokinine) inside the plant. Recent work indicate that the appearance of that kind of symptom might be connected with the matrix potential of the medium (DEBERGH et al, 1981). Other authors confirm the predominant role that the $NH_4^+$ ion allegedly plays, perhaps in correlation with other elements, in the appearance of that phenomenon (BEAUCHESNE, 1981).

Other observations have been made by different authors concerning techniques that make it possible to eliminate or at least to reduce the severity of those symptoms. ZUCCHERELLI (1979) points out that the addition of food pectin to the culture medium might reduce the occurrence of "vitereous" plants. DRUART (1980) indicates that the passage of plant material into a cold chamber at more or less 2° C. for about one month allegedly restricts the appearance of such symptoms.

"However, those findings do not make it possible to explain wholly this phenomenon, which is probably very complex as a result of the number of factors that can be involved."

Agar is presently used in culture media, usually in amounts of 7 to 12 g/l, in order to solidify the media. This facilitates the arrangement of plants and reduces to a certain extent the risks of vitrification. However, the rate of multiplication is always higher in a liquid medium than it is in a solid medium, especially when the amount of agar is greater than about 7 g/l. The solutions recommended thus far have only brought a very limited solution to vitrification, with the symptoms re-emerging after 2 or 3 multiplications (generations) on the recommended improved medium.

With respect to DEBERGH's (Physiol. Plant 59.270-276, 1983) recommendation to increase the amount of agar in the solid medium, this approach can protect microcuttings or microplants from vitrification, but it leads to a very high reduction of the rate of multiplication. The effect of agar in this instance is simply to increase the matrix potential of the medium.

This approach is very different from the approach used in the present invention in which a liquid medium is used. The present invention uses a null matrix potential. Furthermore, increasing the amount of agar augments the solid feature of the culture medium, and reduces contact between the microcuttings or microplants and the culture medium. This diminishes even more the rate of multiplication. The relative "protection" against vitrification is obtained to the considerable detriment of multiplication rate.

There is therefore a strongly felt need for a solution to the problem of "vitrification", "vitrescence" or "hyperhydria" found in the in vitro multiplication of plants, where such a solution does not act to the detriment of the multiplication rate of the plants being grown.

SUMMARY OF THE INVENTION

Accordingly, it is one object of this invention to provide a solution to the problem of vitrification in the in vitro multiplication of plants.

It is another object of this invention to provide a solution to the problem of vitrescence in the in vitro multiplication of plants.

It is another object of this invention to provide a solution to the problem of hyperhydria in the in vitro multiplication of plants.

It is another object of this invention to provide a solution to each of the above problems without effecting detrimentally the rate of multiplication of the plants being multiplied in vitro.

The present inventors have now discovered a novel composition for fighting growth disturbances found in the micropropagation of plants multiplied in vitro. This process satisfies all of the above objects of this invention and other objects which will become apparent from a reading of the description of the invention given hereinbelow. This process which combats growth disturbances known as vitrification, vitrescence or hyperhydria in the micropropagation of plants multiplied in vitro is characterized by the fact that it involves incorporation of an effective amount of agar hydrolysate in the culture medium used to multiply the plants.

DETAILED DESCRIPTION OF THE PREFERRED EMBODIMENTS

As discussed above, one of the purposes of the invention is to provide a solution to vitrification disturbances without loss of the rate of plant multiplication. One characteristic of this invention therefore provides a method to fight against growth disturbances, referred to as vitrification, vitrescence or hyperhydria, in the micropropagation of plants that are multiplied in vitro. In this method one incorporates an efficient amount of agar hydrolysate in the culture medium used to grow the plants.

In a preferred embodiment of the invention, the amount of agar hydrolysate used in the culture medium equals at least 0.1 g/l (calculated on the basis of agar before hydrolysis) of nutritional medium. The amount of agar hydrolysate which can be used ranges from 0.1 g/l to 100 g/l. And even higher amounts of agar hydrolysate can be used.

In another embodiment the invention provides a composition for fighting the vitrification of plants that are multiplied by way of in vitro micropropagation. This composition contains an agar hydrolysate acting as an active principle. The agar hydrolysate can be used in a range of from 0.1 g/l to 500 g/l, preferably 0.1 g/l to 100 g/l, of culture medium.

Another embodiment of this invention provides a process for preparing the composition discussed above. In this process one hydrolyzes agar in an acid medium, at a temperature of between 20 and 200° C., for a period of time of from 10 minutes to 7 days. Preferably, the hydrolysis is performed at a temperature between 100 and 120° C., for 30 to 60 minutes, at pH=3 to 4.

The acid medium used for the hydrolysis can be acifified water or an acidified culture medium. The choice between these two materials as acid medium depends on whether one wishes to obtain a pure agar hydrolysate which can be added to a culture medium, or to prepare directly the culture medium which contains agar hydrolysate therein in a desired amount.

In a preferred embodiment of the invention one introduces into the nutritional medium an effective amount of agar hydrolysate. According to tests that were conducted by the inventors, the amount of agar hydrolysate is not critical, as long as it is greater than 0.1 g/l (calculated on the basis of agar before hydrolysis) of nutritional medium, a threshold under which no activity has been observed.

The invention applies to all the plant species. It especially applies to the ligneous species, including in particular Prunus and Malus from among the fruit trees, for which the inventors have a vitrification induction method, and especially for which exemplary embodiments are provided. The present invention is also advantageously applied to nonligneous species however.

Agar hydrolysate is liquid. Therefore it does not solidify the culture medium. Multiplication in the present invention occurs in a liquid medium, in other words, under the most favorable conditions from the standpoint of the rate of multiplication, but with a greater risk that plant vitrification will appear.

The agar is hydrolyzed, either alone in water, or with the liquid culture medium.

Any culture medium well known in the art can be used with this invention. For example, medium recommended by DRUART (International Colloquium on in vitro culture of wood essences, pp. 101-108, 1981, IUFRO Fontainebleau, France) can be advantageously used.

The vitrification induction model recommended by PAQUES (Arch. Int. Phys. et Bioch. 1984, 92, 20), which uses a liquid medium in which the bases of stems from microplants are submerged, can act as an activity efficiency control for the agar hydrolysate.

One implementation of the invention involves the introduction of agar in the selected culture medium, as if one were preparing a solid conventional culture medium, in the amount of 0.1 to 100 g/l.

Then, the unit is hydrolyzed in an acid medium, pH=0 to 7, preferably pH=0 to 4, more preferably pH=3 to 4, at a temperature in the 20-200° C. range, preferably 50-150° C, more preferably 75-120° C., for periods of time that vary as a function of the temperature and the pH used and which are typically from 10 minutes to 7 days. The acid used for acidification is not a parameter of the invention, and any ordinary acid can be used as long as it does not interfere with the multiplication process. For instance hydrochloric acid, sulfuric acid, phosphoric acids, carboxylic acids and analogues can be used.

A preferred hydrolysis according to the invention involves hydrolysis at pH 3-4, at a temperature of 75 to 120° C. Hydrolysis lasts between 30 and 40 minutes.

The hydrolysate that is obtained, or the floating remainder stemming from centrifuging, is used then as a culture medium. Indeed, tests have shown that the centrifuging base was inert, and did not play a role in the process of fighting against vitrification according to the invention. Therefore, if so desired, it can be eliminated for the sake of convenience.

Hydrolysis of the culture medium is not useful however according to the invention and one can also prepare a "pure" agar hydrolysate, in other words free of culture medium. Thus, one can prepare a concentrated hydrolysate, for instance by adding to the agar the amount of water that is strictly needed to achieve hydrolysis. This concentrated hydrolysate can be added then as such to the selected culture medium, in order to protect the plants from the risk of vitrification. Other features of the invention will become apparent in the course of the following descriptions of exemplary embodiments which are given for illustration of the invention and are not intended to be limiting thereof.

In this description, the amounts of agar hydrolysate are given in grams/liter of culture medium, and they refer to the weight of agar before hydrolysis.

As discussed above, the inventors have found that the amount of agar hydrolysate was not a significant parameter of the invention, so long as it is equal to or greater than the efficient amount, or about 0.1 g/l. Preferred amounts are 1 to 100 g/l, better 7 to 12 g/l, or amounts equal to those used presently for solidifying the culture media.

Moreover, the origin of agar does not influence the anti-vitrification properties. The agar used by the inventors is "Bacto" quality agar from DIFCO.

EXAMPLE

Microcuttings of apple-tree M 26 stock are grown either on a liquid proliferation medium which contains an agar hydrolysate, or on the same medium free of that hydrolysate.

The culture media are prepared as follows:

medium with agar hydrolysate: the solution is comprised of macroelements, microelements, vitamins, growth and sucrose substances in concentrations recommended by DRUART (1981). "Bacto" agar from DIFCO is added to a 7 g/l concentration.

medium free of agar hydrolysate: this medium contains all of the previously mentioned elements except for agar.

The pH of the created media is adjusted to 3.5 with hydrochloric acid, at ambient laboratory temperature. Then, the solutions are either brought to boiling, distributed in the culture flasks then sterilized for 40 minutes at 110° C., or directly sterilized under the previously mentioned conditions then distributed sterilely in the culture flasks.

The media thus obtained are liquid, however, the medium which contains hydrolyzed agar flocculates slightly.

The agar-free medium (medium A) is used as such; the medium which contains the agar hydrolysate being used either as such (medium $B_1$), or centrifuged at 300g for 10 minutes. The floating remainder which is obtained comprises the culture medium $B_2$. The base which is suspended again in the agar-free medium is medium $B_3$.

Growth of explants (offshoots)

20 microcuttings of M 26, 2 cm long, are planted on the four nutritional media described above. The recorded observations, after thirty days of culture are listed in the following table:

| OBSERVATIONS | MEDIA | | | |
| --- | --- | --- | --- | --- |
| | A | $B_1$ | $B_2$ | $B_3$ |
| Vitrification rate | 20/20 | 0/20 | 0/20 | 19/20 |
| Number of buds/plant | 4–7 | 5–7 | 6–7 | 5–6 |

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A process for combating vitrification, vitrescence or hyperhydria in the in vitro micropropagation of plants from pre-existing buds, comprising growing the said plants in a culture medium containing an effective amount of agar hydrolysate.

2. The process of claim 1, wherein the said agar hydrolysate is used in an amount of at least 0.1 g/l, calculated on the basis of agar before hydrolysis, relative to the said culture medium.

3. The process of claim 1, wherein the said plant is a ligneous species plant.

4. The process of claim 3, wherein the said ligneous species is Prunus or Malus.

5. The process of claim 1, wherein the said plant is a non-ligneous species.

6. The process of claim 2 wherein said agar hydrolysate is used in an amount of from 0.1 g/l to 100 g/l, calculated on the basis of agar before hydrolysis, relative to the said culture medium.

7. The process of claim 1, wherein said agar hydrolysate is obtained by hydrolyzing agar in an acid medium at a temperature of between 20 and 200° C. for a period of time of from 10 minutes to 7 days.

8. The process of claim 1, wherein said agar hydrolysate is obtained by hydrolyzing agar at a temperature of between 100 and 120° C. for 30 to 60 minutes at a pH of from 3 to 4.

9. The process of claim 1, wherein the said plant is a fruit tree.

* * * * *